United States Patent [19]

Dore et al.

[11] 4,301,551

[45] Nov. 24, 1981

[54] DEFORMABLE HIGH ENERGY STORAGE TENSION SPRING

[75] Inventors: Roland Dore, Montreal; Gilbert Drouin, l'Acadie, both of Canada

[73] Assignee: Ecole Polythechnique, Montreal, Canada

[21] Appl. No.: 56,043

[22] Filed: Jul. 9, 1979

[30] Foreign Application Priority Data

May 24, 1979 [CA] Canada .................................. 328441

[51] Int. Cl.$^3$ .............................................. A61F 1/00
[52] U.S. Cl. .......................................... 3/1; 267/152; 403/223
[58] Field of Search ............... 3/1; 267/153, 152, 148, 267/57.1 R, 57.1A, 154; 64/27 NM, 27 R; 403/223, 221, 222, 225, 226, 228, 229, 291

[56] References Cited

U.S. PATENT DOCUMENTS

| | | | |
|---|---|---|---|
| 3,176,316 | 4/1965 | Bodell | 3/1 |
| 3,806,627 | 4/1974 | Harmon | 267/152 X |
| 3,882,551 | 5/1975 | Helmer et al. | 3/1 |
| 3,953,896 | 5/1976 | Treace | 3/1 |
| 4,149,277 | 4/1979 | Bokros | 3/1 |

OTHER PUBLICATIONS

Drovin, et al., "A New Concept for the Design of Prosthesis for Knee Ligament", July, 1977.
Drovin, et al., "A New Concept for the Design of Prostheses for Ligament Replacements", 1978, *Biomechanics,* vol. VI-A, p. 395.
Wevers, "The Specification and Design of a Substitute Medial Collateral Ligament", Digest of the 11$^{th}$ International Conference on Medical and Biological Engineering; 1976; pp. 494-495.

*Primary Examiner*—Clifford D. Crowder
*Attorney, Agent, or Firm*—Fishman and Van Kirk

[57] ABSTRACT

A tension spring capable of large elastic deformation and having a high resistance to breakage and particularly, but not exclusively, for use as an artificial prosthetic ligament. The spring comprises an elongate elastic core having a low modulus of elasticity and defining opposed ends. A tensionable wrapping of thread having a high resistance to breakage is disposed in contact about the core to compress the core and to cause it to elongate axially upon opposite relative axial displacement of opposed ends of the wrapping secured to traction means.

14 Claims, 7 Drawing Figures

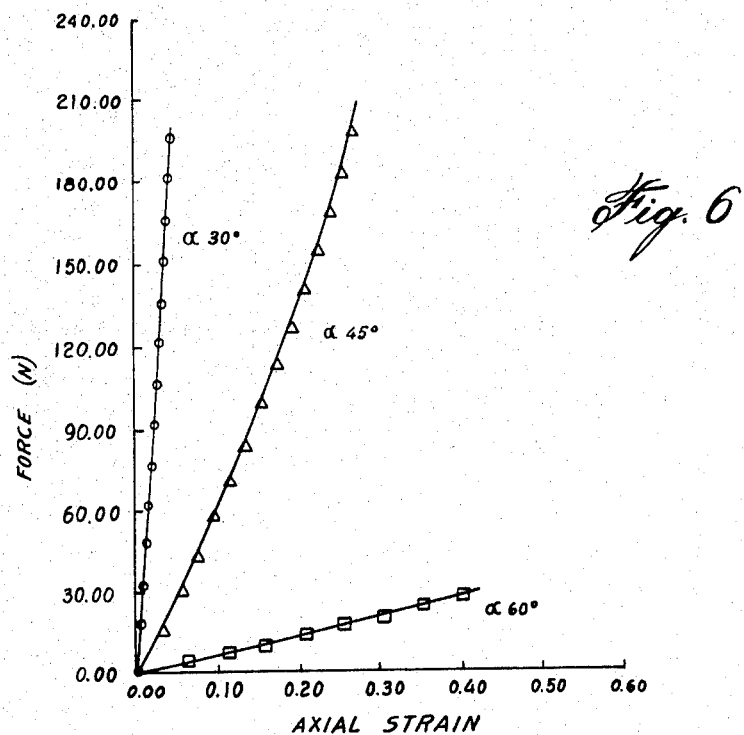
Figure 6 - Computed force/axial strain relation for the theoretical model with helix angle $\alpha$ = 30", 45" and 60"
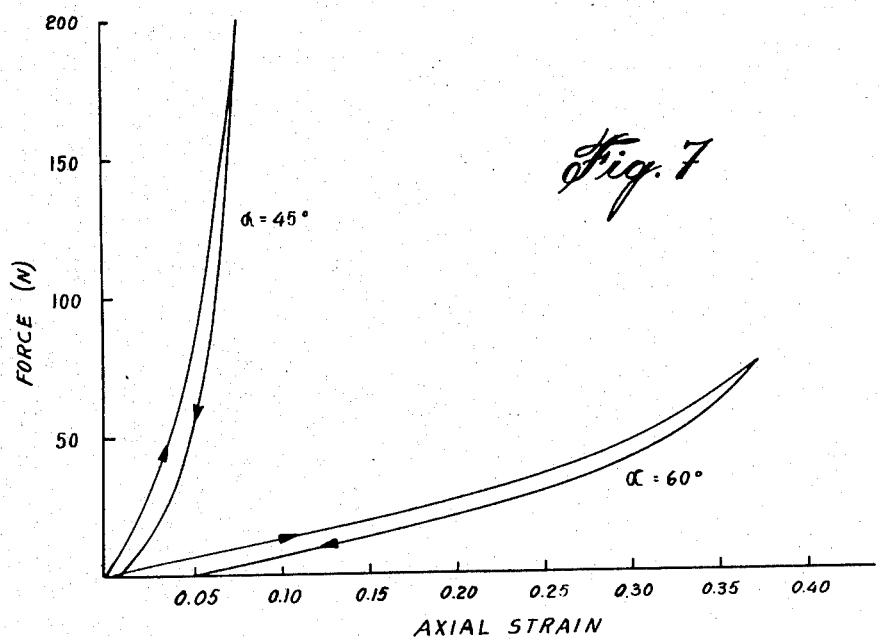
Figure 7 - Recorded force/axial strain relation for two prototypes with helix angle $\alpha$ = 45" and 60", respectively

DEFORMABLE HIGH ENERGY STORAGE TENSION SPRING

BACKGROUND OF THE INVENTION

1. Field of Invention

The present invention relates to a tension spring, and more particularly, but not exclusively, for use as an artificial prosthetic ligament of capable of large elastic deformation and having high resistance to breakage.

2. Description of Prior Art

The ligaments are biologic structures present in all human articulations, where they are used as stabilizers. As such, they must have a high strength coupled with a capacity for large elastic deformation to sustain repetitively the loads imposed on the articulation.

If the loads cause stresses exceeding the strength of the ligaments, it produces a partial or complete rupture of the ligament. Since most ligaments are not vascularized, any partial or complete rupture cannot heal by itself as a muscle or a bone would do. In most cases of complete rupture of the ligament, the clinician must replace the ligament by either biologic materials, (skin, facia, tendon) or by an artificial prosthesis. Known ligament prosthesis heretofore known have not been very successful.

Artificial ligaments were proposed using one biocompatible material. However, the mechanical behavior of the ligament cannot be mimicked by a single material because of the high strength and large elastic deformation required. For a single material the deformation and strength are related through the modulus of elasticity.

A prosthesis made of a single material would give a result that if the strength of the prosthesis is sufficient, its elastic deformation is not. Therefore, the prosthesis suffers a large plastic deformation. If on the other hand, the material is elastic enough, the strength requirement is not met.

Another problem encountered with artificial prosthesis ligaments is that the attachment points of such ligaments in the bones results in a deterioration of the bones at such attachment points.

In U.S. Pat. No. 3,176,316 issued Apr. 6, 1965 to B. R. Bodell, there is disclosed the construction of a plastic prosthetic tendon. However, this construction is not suitable for use as a ligament as it is an inelastic flexible elongated structure and its purpose is to transmit a force with negligible deformation. On the other hand, a ligament is an elastic flexible elongated structure and its purpose is to stabilize an anatomical joint, and as such, it acts as a spring. Therefore, it must deform under load.

Several types of prostheses are presently implanted in the human knee to replace a ruptured cruciate ligament. None of them, however, have reportedly been adequate due to inacceptable plastic deformations after a relatively short period of time. The functional part of these prostheses is usually made of a single synthetic material with adequate strength properties but not allowing sufficient elastic elongation as compared to the natural ligament.

SUMMARY OF THE INVENTION

It is a feature of the present invention to provide a tension spring capable of large elastic deformation and having a high resistance to breakage.

It is a further object of the present invention to provide a tension spring made of two materials and wherein the axial deformation of the spring is obtained by a radial deformation of a soft central core. The high resistance to breakage is obtained by fibers or threads wound about the soft central core.

A further object of the present invention is to provide a tension spring wherein the helix angle of the threads wound about the core is selected to achieve a predetermined characteristic of the spring.

A still further object of the present invention is to provide a tension spring wherein the modulus of elasticity of the core is preselected to achieve a predetermined characteristic of the spring.

A further object of the present invention is to provide a tension spring particularly for use as an artificial prosthesis ligament which can be secured across a joint and attached to bone structure in a manner to minimize deterioration of the bones.

A still further object of the present invention is to provide a novel method of making an artificial prosthesis ligament with a soft central core with threads having high resistance to breakage wound about the core whereby the core provides capacity for large elastic deformation and the threads provide high resistance to breakage.

A further object of the present invention is to provide a novel method of implanting an artificial cruciate ligament between adjacent bones of a knee joint.

According to the above objects, from a broad aspect, the present invention provides a tension spring capable of large elastic deformation and a high resistance to breakage. The spring comprises an elongate elastic core having a low modulus of elasticity and defining opposed ends. A tensionable wrapping of thread having a high resistance to breakage is disposed in contact about the core to compress the core between its opposed ends and to cause it to elongate axially upon opposite relative displacement of opposed ends of the wrapping.

According to a still further broad aspect of the present invention, there is provided an artificial prosthesis ligament capable of large elastic deformation and having a high resistance to breakage and comprising an elongate elastic core having a low modulus of elasticity and defining opposed ends. A tensionable wrapping of thread having a high resistance to breakage is disposed in contact about the core to compress the core between its opposed ends and to cause it to elongate axially upon opposite relative displacement of opposed ends of the wrapping.

According to a still further broad aspect of the present invention, there is provided a method of making an artificial prosthesis ligament comprising the steps of providing an elongate elastic core having a low modulus of elasticity, and helically winding at least two windings about the core of a thread having a high resistance to breakage, the windings of thread having thread windings disposed at substantially the same helix angle.

According to a still further broad aspect of the present invention, there is provided a method of implanting an artificial cruciate ligament between adjacent bones of a knee joint. The method comprises drilling an angularly disposed channel substantially along the axis of a formerly existing human ligament being replaced and extending respectively through the adjacent bones when the knee is in an extension position, the channel being constituted by channel sections in the adjacent bones. Connecting means is secured in the opposite ends of the channel. An artificial prosthesis ligament is disposed in the channel. The prosthesis ligament has an elongate elastic core having a low modulus of elasticity, and a tensionable wrapping of thread having a high resistance to breakage in contact about the core to compress the core between its opposed ends to cause it to elongate axially upon opposite relative displacement of opposed ends of the wrapping. An end connector is attached to a respective one of the opposed ends of the wrapping. The end connectors are secured to a respective one of the connecting means.

BRIEF DESCRIPTION OF THE DRAWINGS

A preferred embodiment of the present invention will now be described with reference to the examples thereof illustrated by the accompanying drawings in which:

FIG. 6 is a graph of force/axial strain curves computed for theoretical models; and FIG. 7 is a graph of force/axial strain curves, loading and unloading, of two actual artificial prosthesis ligaments constructed in accordance with the present invention.

DESCRIPTION OF PREFERRED EMBODIMENT

Figure 1:
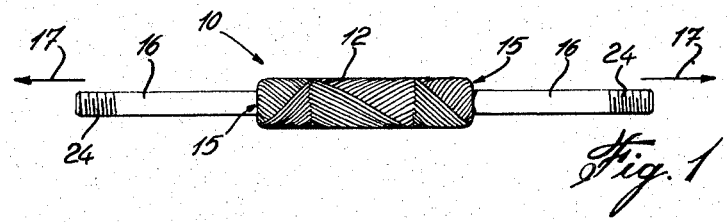
FIG. 1 is a plan view of the artificial prosthesis ligament or tension spring of the present invention.
Figure 2:
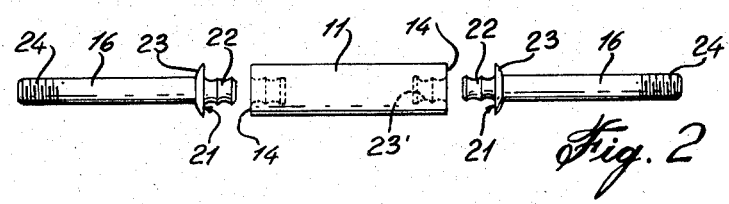
FIG. 2 is an exploded view showing the elastic core and the end connectors of the prosthesis ligament.
Figure 3:
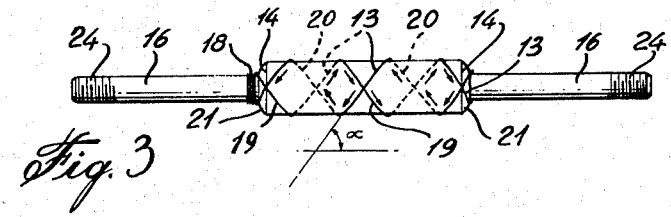
FIG. 3 is a plan view illustrating the thread windings forming the sleeve having a high resistance to breakage.

Referring now to the drawings, and more particularly to FIGS. 1 to 3, there is shown generally at 10, the tension spring of the present invention. Hereinafter, this tension spring will be described with reference to one of its applications as an artificial prosthesis ligament.

As herein shown, the artificial prosthesis ligament 10 consists essentially of an elongate elastic core 11 made of a material having a low modulus of elasticity, and a tensionable wrapping 12 disposed in contact thereabout. The wrapping 12 is formed by a plurality of overlapping layers or windings of helically wound thread 13 having high resistance to breakage disposed alternately in opposed directions about the core 11 and between opposed ends 14 of the core. The wrapping is provided with opposed connectible ends 15, herein shown secured to a respective end connector 16 whereby when the end connectors are displaced in a direction away from one another, as illustrated by arrows 17, the helical windings of thread will tend to assume a shallower helix angle α and result in a compression of the elastic core 11. Accordingly, the elastic core will be compressed and elongate axially. As shown in FIG. 1, the connectible ends 15 are constituted by winding the thread windings over the shoulder 23 of the retention means 21 of the connectors 16, as described later with reference to FIGS. 2 and 3. The connectors 16 constitute traction means to pull opposed ends 15 of the wrapping away from one another to compress the core 11.

The core 11 is made of silicone or other suitable material capable of large elastic deformation and the threads are selected from suitable materials having high resistance to breakage, such as surgical threads or stainless steel wire, and these are coated with a silicone, or other suitable coating, after they have been wound about the core for maintaining the threads in place and protecting them. As herein shown, the windings of the wrapping are woven with one another whereby to be maintained in place.

It can therefore be seen that the axial deformation of the prosthesis is obtained by the soft central core while the high strength or large resistance to breakage thereof is provided by the thread windings. Since these two materials can be chosen independently, the behavior of the ligament to be artificially reproduced can be achieved.

Referring now specifically to FIG. 3, there is shown the winding of the thread about the core to form the wrapping 12. As herein shown, a continuous thread 13 is wound around the core at a predetermined helix angle α. One end of the thread is attached to the end connector 16, such as at 18, and a first winding 19 is wound from opposed ends 14 of the core. The thread winding is then reversed at the other end to form a second winding 20 extending at the same helix angle α, but in opposed direction. These windings are continued from end-to-end of the core and about a sleeve retention means 21 of the rod 16 until enough winding of the thread is provided to resist the intended applied load.

It can be seen that the larger the angle α is, the more elongate deformation that can be transferred to the elastic core. As the angle α becomes shallower or smaller, the rate of compression of the core diminishes, resulting in less elongate deformation. Thus, the axial deformation can be controlled. The resistance to breakage is controlled by the composition of the thread 13 and the number of windings about the core 11.

Referring now more specifically to FIG. 2, there is shown the construction of the end connectors 16. The end connectors are constituted by a rigid metallic rod or a rod constructed of any suitable rigid material, such as rigid plastics, and is provided with an anchor end 22 adapted to be anchored in the opposed ends 14 of the core. As herein shown, the ends 14 of the core may be provided with a securing cavity 23' (may be threaded) configured to receive and retain the anchor end 22 (may be threaded) of a respective rod 16. The rod also defines a wrapping retention means 21, herein constituted by a shoulder extending about the rod, adjacent the anchor end 22. This shoulder abuts the respective one of the opposed ends 14 of the core, and the thread 13 is wound about the shoulder whereby to secure the rod and core together and at the same time, provide for the shoulder 23 to transmit an axial load on the rod 16 directly to the wrapping 12 from the opposed connecting ends 15 of that wrapping. The rod is also provided with a securable free end, herein a helical thread 24, to secure the prosthesis.

Figure 4:
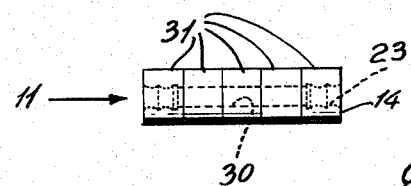
FIG. 4 is a plan view of the elastic core showing modifications thereto.

Referring now to FIG. 4, there is shown various modifications or constructions of the core 11. As herein shown, the core is provided with a through bore 30 with the securement cavities 23' formed at respective opposed ends of the through bore 30. It can be seen that by varying the size of the through bore, the elastic property of the core can be varied. Also, a liquid (not shown) may be provided in the through bore intermediate the anchor ends 22 of the rod 16 whereby to constitute an absorber in the core. The anchor ends 22 would form seals at the respective ends of the through bore to prevent leakage of the liquid. Instead of a through bore filled with liquid, the core could also be made of a plastics material impregnated with liquid molecules (gel material).

Furthermore, the core 11 may be made from a plurality of cylinder-shaped elastic elements 31 positioned side-by-side axially and retained in this configuration by the wrapping and the connecting rod 16. The cylinder-shaped elements 31 at opposed ends of the wrapping would have the connector rod 16 secured thereto.

It can be seen by constructing a prosthesis ligament as above described, that the combination of the two elements, that is, the core and the wrapping, ensures the behavior of the artificial ligament that neither of the two materials could have by themselves. The resistance to breakage and elasticity of the artificial ligament can be calculated, taking into consideration the following variables, and namely: the length of the prosthesis (L), the diameter (D, Di) and the material of the core (E(p)), the diameter (d), the material (E$_f$) and the number of threads (n) and the helix angle ($\alpha$) of the windings. These variables are calculated to produce the desired elongation under a given load, geometrical constraints and a margin of safety. As for natural ligaments, the stiffness of such a device is increasing with deformation.

Based on the above variables, a mathematical model was developed. In order to derive a relationship between tensile force and elongation for this new type of prosthesis it is assumed that (1) the spatial frequency of the fibers is high enough for the core to be considered under uniform radial compression; (2) the core material has a non-linear elastic behavior while the fiber material is linearly elastic; (3) the plane strain hypothesis holds for the core, i.e. end effects and friction between fibers and core can be neglected; and (4) the changes in the helix angle due to loading can be neglected in the equilibrium and compatibility equations. The above assumptions limit the application of this mathematical model to small deformations.

Force/Elongation Relationship:

If a force F, applied to the composite prosthesis, is equally divided among n fibers wound helically around the core with an angle $\alpha$ and if bending stresses are neglected, it can be shown that each fiber of diameter d will be axially loaded with a tensile force ($T_f$), $$T_f = \frac{F}{n \cos \alpha} \quad (1)$$

This will in turn generate a corresponding fiber axial strain ($\epsilon_f$), $$\epsilon_f = \frac{4F}{\pi d^2 E_f n \cos \alpha} \quad (2)$$

where E$_f$ is the Young's modulus of the fiber material. If the fibers are assumed to exert uniform pressure on the core material, the resulting radial pressure P on a cylindrical core of external diameter D will be $$P = \frac{2F \tan^2 \alpha}{\pi D^2} \quad (3)$$

The core material properties are assumed to be fully specified by its Poisson's ratio $\nu$ and a pressure dependent Young's modulus, E(p). In the case of hollow cylinder of internal diameter D$_i$, assuming the pressure in the cylinder bore to be zero, the radial strain $\epsilon_c$ at the periphery can be expressed by the following equilibrium equation, $$\epsilon_c = \left( \frac{D^2 + D_i^2}{D^2 - D_i^2} - \nu \right) \cdot \int_0^P \frac{dp}{E(p)} \quad (4)$$

To preserve the structural continuity of the device under axial loading, the overall axial ($\epsilon$) and radial ($\epsilon_c$) strains must satisfy a compatibility equation, which for small deformations can be shown to be $$\epsilon = \frac{\epsilon_f}{\cos^2 \alpha} + \epsilon_c \tan^2 \alpha \quad (5)$$

By introducing (2), (3) and (4) into (5) the force/elongation relationship for a model of given length L is $$\Delta L = \epsilon L = \frac{4FL}{E_f \pi d^2 n \cos^3 \alpha} + \quad (6)$$

$$\left( \frac{D^2 + D_i^2}{D^2 - D_i^2} - \nu \right) L \int_0^{\frac{2F \tan^2 \alpha}{\pi D^2}} \frac{dp}{E(p)}$$

where $\nu$ is the Poisson ratio of the material and $\Delta L$ is the elongation of the prosthesis. To illustrate the behavior of equation (6) we will refer to a theoretical and practical example using such parameters as the helix angle $\alpha$ of the fibers and the non-linearity of the core material properties, a computation of the force/elongation relationship has been performed with the use of an exponential form for the pressure dependent Young's modulus of the core material, $$E(p) = (e^{ap}/a) \quad (7)$$

where 1/a is the Young's modulus of the unstressed material. It is noted that equation (7) is not the only workable function of E(p). In this particular case, after integration, (6) reduces to $$\epsilon = \frac{\Delta L}{L} = \frac{4F}{E_f \pi d^2 n \cos^3 \alpha} + \quad (8)$$

$$\tan^2 \alpha \left( \frac{D^2 + D_i^2}{D^2 - D_i^2} - \nu \right) \left( 1 - e^{\frac{-2aF \tan^2 \alpha}{\pi D^2}} \right)$$

Referring now to FIG. 6, there is shown the force/axial strain curves computed for three different helix angles, namely $\alpha = 30°$, 45° and 60° for a model having the following dimensions and material properties:

L = 100 mm, D = 10 mm, D$_i$ = 1.5 mm, $\nu$ = 0.49, E(p) = 2e$^{0.5p}$ MPa, n = 100, d = 1 mm and E$_f$ = 700 MPa.

Several prototypes have been built and tested to verify the validity of the mathematical model proposed, particularly to investigate the influence of the helix angle of winding of the fibers on the force/elongation relationship. FIG. 7 illustrates the force/axial strain loading and unloading curves obtained on an Instron universal testing machine at crosshead speed of 20 mm/min with two prototypes made of 2-0 Tevdek II* Teflon*-impregnated Dacron* synthetic suture (Deknatel, Inc.) wound 150 times at 45° and 60° angles, respectively, around a hollow cylindrical core of Silastic* 382 Medical Grade elastomer (Dow Corning, Ltd.) of dimensions L = 80 mm, D = 12.7 mm and D$_i$ = 2.3 mm.

*Trademark

The experimental curves of FIG. 7 are in good agreement with those of FIG. 6 computed for the theoretical model, in particular in terms of the influence of the fiber helix angle on the force/axial strain relationship.

In an article "Functional and Dynamic Characterization of Canine Lateral Cruciate Ligaments", First Int. Conference on Mechanics in Med. and Biol., Aachen, Dorlot, et al (1978), have compiled an average load/strain diagram for the canine lateral cruciate ligament within its functional range. They report that the response has a non-linear concave shape with an average strain of 0 to 0.14 for a load of 0 to 200 N. It can be observed that by adjusting properly the helix angle of the fibers in the two-material composite device, a close approximation of the natural ligament behavior may be obtained.

The method of making the artificial prosthesis ligament is as follows. An elongate elastic core, having a low modulus of elasticity, is provided, and a continuous thread is then wound around the core at a helix angle $\alpha$. It is pointed out that every winding from opposed ends 14 of the core 11 could be constituted by an individual thread which is conveniently secured to the shoulder 23 of the connecting rod 16 or other connecting means. However, in this embodiment, the windings are constituted by a single thread wound from end-to-end of the core. This process is continued until there are enough fibers wound about the soft core so that the spring or prosthesis ligament can resist the load to be applied. It is pointed out that the soft core 11 need not be fixed to the end connector 16 but the ends of the thread windings should, as the axial load on the connector rod 16 must be transferred to the wrapping to obtain the above-mentioned desired results.

Figure 5:
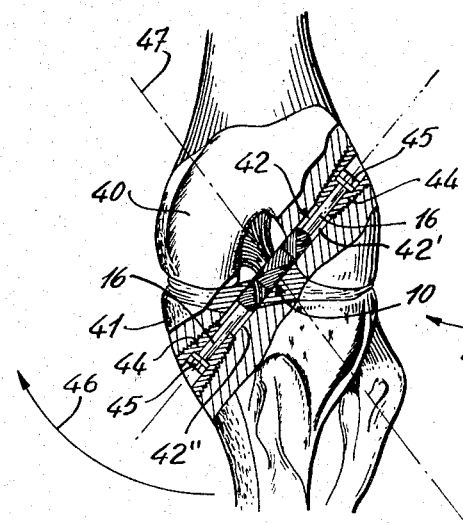
FIG. 5 is a fragmented section view showing an implanted artificial prosthesis ligament of the present invention replacing a cruciate human ligament between adjacent bones of a knee joint.

Referring now to FIG. 5, there is shown the artificial prosthesis ligament 10 implanted between adjacent bones 40 and 41 of a knee joint 42. The implantation is achieved by drilling an angularly disposed channel 42 substantially along the axis of a formerly existing human ligament being replaced and extending respectively through the adjacent bones 40 and 41 whereby to constitute axially aligned channel sections 42' and 42" when the knee is in an extension position. Connecting means, herein a threaded plug 44, is secured in the opposed ends of the channel sections 42' and 42", to secure the securing free ends 24 of the connecting rods 16 to their respective bones 40 and 41. With the prosthesis ligament located in the channel and the rods 16 secured to their respective bones by means of a securement nut 45 or other convenient means, the bones are biased towards one another and may flex with respect to one another in their normal operating manner as indicated by arrow 46. The axis 47 holds the position of the second cruciate ligament at the knee joint and it is disposed in a laterally spaced position from the artificial prosthesis ligament 10 and extends in opposition thereto.

As hereinabove described, the tension spring of the present invention has specific application for artificial prosthesis ligament, but should not be restricted thereto. This spring could be substituted for devices subjected to large deformation, high stresses and constrain to a small volume (i.e. tension springs). Furthermore, the tension spring could constitute a flexible shaft or a spring shock absorber, and thus has many applications. The spring of the present invention has the advantages of being easy to manufacture, using conventional winding processes, has a high resistance to breakage in a relatively small volume, provides high energy storage capacity in a relatively small volume, also provides high rigidity in a small volume. The spring further provides easy variation of the load versus deformation curve of the spring by varying the design parameters of the spring: material of the thread (fiber or filament), material of the core, helix angle of the winding, number of windings, diameter of the core, diameter of the thread, and length of the spring.

It is within the ambit of the present invention to encompass any obvious modifications of the preferred embodiment illustrated by the accompanying drawings, provided such modifications fall within the scope of the appended claims.

We claim:

1. An artificial prosthetic ligament capable of large elastic deformation and high resistance to breakage comprising an elongate elastic core having a low modulus of elasticity and opposed ends, a tensionable wrapping formed of threads having a large resistance to breakage is provided in contact about said core, said wrapping being constituted by at least two windings of helically wound thread having large resistance to breakage and a high modulus of elasticity as compared to that of the core, said windings being disposed in alternate opposed directions to one another and having substantially the same helix angle, said core being elongated axially by compression force applied by said wrapping caused by opposite relative axial displacement of opposed ends of said wrapping secured to traction means, said elongation being determined by the mathematical expression:

$$\Delta L = \epsilon L = \frac{4FL}{E_f \pi d^2 n \cos^3 \alpha} + \left( \frac{D^2 + D_i^2}{D^2 - D_i^2} - \nu \right) L \int_0^{\frac{2F \tan^2 \alpha}{\pi D^2}} \frac{dp}{E(p)}$$

where $\nu$ is the Poisson ratio of the material, $\Delta L$ is the elongation of the prosthesis, $E_f$ is the Young's modulus of the fiber material, D is the external diameter of the core, $D_i$ is the internal diameter of the core, $\alpha$ is the helix angle, L is the length of the prosthesis, E(p) is the elastic modulus function of the core, n is the number of threads, $\epsilon$ is the axial strain for a given length L, F is the tensile force, and d is the thread diameter.

2. An artificial prosthetic ligament as claimed in claim 1 wherein said wrapping is constituted by a plurality of said windings, said helix angle being selected to achieve a predetermined axial deformation of said core when said relative displacement occurs, said windings being of sufficient quantity to achieve a predetermined desired axial resistance to breakage, each said windings being constituted by a continuous thread.

3. An artificial prosthetic ligament as claimed in claim 1, wherein there is further provided an end connector at each said opposed ends of said core, said opposed ends of said wrapping being attached to a respective end connector.

4. An artificial prosthetic ligament as claimed in claim 3, wherein said end connector is a rigid rod having an anchor end for housing in an end cavity of said core located at each said opposed ends of said core, a wrapping retention means, and a securable free end.

5. An artificial prosthetic ligament as claimed in claim 4, wherein said wrapping retention means is a shoulder about said rod adjacent said anchor end, said connectible opposed ends of said wrapping being constituted by winding said thread about a respective rod at each end of said core and over said shoulder of each said rod.

6. An artificial prosthetic ligament as claimed in claim 5, wherein said securable free end is a threaded end for threaded engagement with a securement element.

7. An artificial prosthetic ligament as claimed in claim 3, wherein said core has a through bore, said end connectors being secured at a respective end of said through bore.

8. An artificial prosthetic ligament as claimed in claim 7, wherein a liquid is provided in said through bore intermediate said end connectors to constitute an absorber, said end connectors forming seals at said respective end of said through bore to prevent leakage of said liquid.

9. An artificial prosthetic ligament as claimed in claim 3, wherein a liquid is impregnated in said core.

10. An artificial prosthetic ligament as claimed in claim 3, wherein said core is a plurality of cylinder-shaped elastic elements, said elements being maintained in side-by-side relationship by said wrapping, each cylinder-shaped elastic element at opposed ends of said wrapping having said end connector secured thereto.

11. An artificial prosthetic ligament as claimed in claim 1, wherein said thread is coated with silicone or the like material.

12. A method of making an artificial prosthetic ligament comprising the steps of (i) providing an elastic core having a low modulus of elasticity, (ii) helically winding at least two windings of a thread having a large resistance to breakage about said core, said windings extending in opposed directions with their thread windings disposed at substantially the same helix angle, said windings constituting a wrapping having opposed ends, (iii) displacing said opposed ends in opposite axial directions by traction means for compressing said core to cause it to elongate, the elongation being determined by the mathematical expression:

$$\Delta L = \epsilon L = \frac{4FL}{E_f \pi d^2 n \cos^3\alpha} + \left(\frac{D^2 + D_i^2}{D^2 - D_i^2} - v\right) L \int_0^{\frac{2F\tan^2\alpha}{\pi D^2}} \frac{dp}{E(p)}$$

where $v$ is the Poisson ratio of the material, $\Delta L$ is the elongation of the prosthesis, $E_f$ is the Young's modulus of the fiber material, D is the external diameter of the core, $D_i$ is the internal diameter of the core, $\alpha$ is the helix angle, L is the length of the prosthesis, E(p) is the elastic modulus function of the core, n is the number of threads, $\epsilon$ is the axial strain for a given length L, F is the tensile force, and d is the thread diameter.

13. A tension spring capable of large elastic deformation and high resistance to breakage comprising an elastic core having a low modulus of elasticity and opposed ends, a tensionable wrapping formed of threads having a large resistance to breakage is provided in contact about said core to compress said core between its opposed ends and to cause it to elongate axially upon opposite relative axial displacement of opposed ends of said wrapping secured to traction means, said wrapping is constituted by at least two windings of helically wound thread having a large resistance to breakage and a high modulus of elasticity as compared to that of the core, said windings being disposed in alternate opposed directions to one another and having substantially the same helix angle, said helix angle being selected to achieve a predetermined axial deformation of said core when said relative displacement occurs, said axial elongation of said core being determined by the mathematical expression:

$$\Delta L = \epsilon L = \frac{4FL}{E_f \pi d^2 n \cos^3\alpha} + \left(\frac{D^2 + D_i^2}{D^2 - D_i^2} - v\right) L \int_0^{\frac{2F\tan^2\alpha}{\pi D^2}} \frac{dp}{E(p)}$$

where $v$ is the Poisson ratio of the material, $\Delta L$ is the elongation of the prosthesis, $E_f$ is the Young's modulus of the fiber material, D is the external diameter of the core, $D_i$ is the internal diameter of the core, $\alpha$ is the helix angle, L is the length of the prosthesis, E(p) is the elastic modulus function of the core, n is the number of threads, $\epsilon$ is the axial strain for a given length L, F is the tensile force, and d is the thread diameter.

14. A tension spring as claimed in claim 13, wherein said wrapping is constituted by a plurality of said windings, said windings being of sufficient quantity to achieve a predetermined desired axial resistance to breakage, each said windings being constituted by a continuous thread.

* * * * *